`US005473089A`

United States Patent [19]
Gutsche et al.

[11] Patent Number: 5,473,089
[45] Date of Patent: Dec. 5, 1995

[54] PROCESS FOR THE PRODUCTION OF AMMONIUM FATTY ACID HYDROXYALKANESULFONATES

[75] Inventors: Bernhard Gutsche, Hilden, Germany; Timothy J. Cassady, Hamilton, Ohio; Lutz Jeromin; Gerhard Wollmann, both of Hilden, Germany; Norman Milstein, Montgomery, Ohio; Hans-Christian Raths, Monheim, Germany

[73] Assignee: Henkel Kommanditgesellschaft auf Aktien, Duesseldorf, Germany

[21] Appl. No.: 227,846

[22] Filed: Apr. 14, 1994

[51] Int. Cl.$^6$ .................................................. G07B 45/00
[52] U.S. Cl. .............................. 554/92; 554/85; 554/167
[58] Field of Search ........................ 554/85, 92, 167

[56] References Cited

U.S. PATENT DOCUMENTS

| | | | |
|---|---|---|---|
| 4,515,721 | 5/1985 | Login et al. | 260/400 |
| 4,536,338 | 8/1985 | Urban et al. | 260/400 |

FOREIGN PATENT DOCUMENTS

| | | |
|---|---|---|
| 0176330 | 4/1980 | European Pat. Off. |
| 0073626 | 3/1983 | European Pat. Off. |

OTHER PUBLICATIONS

Happi, 18(3), 68 (1981).
Happi, Sep., 1984, 56.
Bull. Chem. Soc. Japan, 43, 2236–2240 (1970).

*Primary Examiner*—José G. Dees
*Assistant Examiner*—Deborah D. Carr
*Attorney, Agent, or Firm*—Ernest G. Szoke; Wayne C. Jaeschke; John E. Drach

[57] ABSTRACT

Ammonium fatty acid hydroxyalkanesulfonates are made by a process in which (a) ammonium hydroxyalkanesulfonate corresponding to general formula (I):

$$HO\text{—}(C_nH_{2n})\text{—}SO_3NH_4 \qquad (I)$$

wherein n=2 to 4, is subjected to the esterification reaction with a fatty acid corresponding to the formula (II)

$$R\text{—}COOH \qquad (II)$$

wherein RCO is an aliphatic, linear or branched acyl radical containing 6 to 18 carbon atoms, in the presence of an esterification catalyst, characterized in that (a) before the esterification reaction, the starting compounds corresponding to formulae (I) and (II) are dried at a temperature of 120° C. to 160° C. and under a pressure of 100 to 700 mbar; (b) the esterification reaction is carried out at a temperature above 160° C. to 195° C. and under a pressure of 250 mbar to atmospheric pressure; (c) water of solution and water of reaction formed are directly removed from the reaction mixture; (d) the catalyst is neutralized with a base on completion of the reaction.

20 Claims, No Drawings

PROCESS FOR THE PRODUCTION OF AMMONIUM FATTY ACID HYDROXYALKANESULFONATES

BACKGROUND OF THE INVENTION

1. Field of the Invention

This invention relates to a process for the production of ammonium fatty acid hydroxyalkanesulfonates in which an ammonium hydroxyalkanesulfonate and a fatty acid containing 6 to 18 carbon atoms are condensed at elevated temperature.

2. Description of the Related Art

Fatty acid hydroxyalkanesulfonic acid salts, more particularly fatty acid isethionates in the $C_{12-14}$ chain length range, are anionic surfactants with only minimal sensitivity to hardness, high foaming and wetting power and excellent compatibility with the skin. More particularly, they are distinguished by the fact that the skin can be cleansed without overly drying out. In addition, the soaps containing these compounds can even be used by people unable to tolerate typical high pH soaps. Accordingly, these compounds are used in cosmetic preparations and cleansing formulations.

In the main, only processes for the production of sodium salts of fatty acid hydroxyalkanesulfonic acids are known from the prior art.

European patent application EP-A-0 073 626 describes a process for the production of fatty acid isethionates. In this process, an aqueous sodium isethionate solution is initially introduced together with a catalyst, which is a combination of ZnO with a sulfonic acid, and the fatty acid is subsequently added. The condensation reaction is carried out with an excess of fatty acid. To obtain a product of high activity, the excess free fatty acid is removed from the reaction mixture on completion of the reaction.

EP-A-0 176 330, for example, describes a mild cleansing composition containing sodium isethionate and fatty acid soap in addition to fatty acid isethionate. To produce this composition, the principal components are combined in the form of an aqueous solution at 100° to 110° C. and are mixed in a mixer at a high shear rate. The mixture is then dried to the required moisture content and made up.

The processes mentioned above give high yields of, above all, the sodium salts of fatty acid hydroxyalkanesulfonic acids. However, the sodium salts produced have the disadvantage that they are very sparingly soluble in water and, accordingly, are unsuitable for clear liquid formulations. In contrast to the sodium salt, the ammonium salt is distinguished by good solubility in water. In addition, it is a very mild, high-foaming surface-active agent which has proved to be particularly kind to the skin. Unfortunately, the processes described above cannot be applied to the production of the corresponding ammonium salts. The ammonium salts differ from the sodium salts in their solubility in water, in their high foaming capacity and in their thermal instability. On account of the high foaming power of ammonium hydroxyalkanesulfonates, more particularly in aqueous solution, it is difficult to carry out the process at low fatty acid contents because the reaction mixture overfoams and becomes uncontrollable. Another difficulty is that the reaction temperature is near the decomposition point of the compound so that the reaction products can very easily become dark in color. There is no known process for the production of these ammonium salts on an industrial scale.

The problem addressed by the present invention was to provide a process which could even be used on an industrial scale for the production of ammonium fatty acid hydroxyalkanesulfonates without any process-related difficulties arising and which would enable ammonium fatty acid hydroxyalkanesulfonates to be obtained in high yields and in a light color.

DESCRIPTION OF THE PREFERRED EMBODIMENTS

Other than in the claims and in the operating examples, or where otherwise indicated, all numbers expressing quantities of ingredients or reaction conditions used herein are to be understood as modified in all instances by the term "about".

The present invention relates to a process for the production of ammonium fatty acid hydroxyalkanesulfonates in which (a) ammonium hydroxyalkanesulfonate corresponding to general formula (I):

$$HO-(C_nH_{2n})-SO_3NH_4 \qquad (I)$$

wherein n=2 to 4, is subjected to the esterification reaction with a fatty acid corresponding to the formula (II)

$$R-COOH \qquad (II)$$

wherein RCO is an aliphatic, linear or branched acyl radical containing 6 to 18 carbon atoms, in the presence of an esterification catalyst, characterized in that (a) before the esterification reaction, the starting compounds corresponding to formulae (I) and (II) are dried at a temperature of 120° C. to 160° C. and under a pressure of 100 to 700 mbar; (b) the esterification reaction is carried out at a temperature above 160° C. to 195° C. and under a pressure of 250 mbar to atmospheric pressure; (c) water of solution and water of reaction formed are directly removed from the reaction mixture; (d) the catalyst is neutralized with a base on completion of the reaction.

The ammonium hydroxyalkanesulfonate (I) used is a compound in which $R^1$ is an alkylene group containing 2 to 4 carbon atoms, more particularly an ethylene group. The ammonium hydroxyalkanesulfonate may be used either as a solid or in the form of an aqueous solution. The aqueous solution is preferably an approximately 50 to 65% by weight aqueous ammonium hydroxyalkanesulfonate solution and, more preferably, a 57 to 60% by weight solution. Where aqueous solutions are used, they contain only a very small percentage of ethylene glycol (0 to 0.8% by weight and preferably 0 to 0.5% by weight) and a small percentage of ammonium sulfate and ammonium bisulfate (0 to 1.0% by weight and preferably 0 to 0.5% by weight) in order to minimize the degree of secondary reaction.

The fatty acid corresponding to general formula (II), $R^2COOH$, used as starting compound is selected from the group consisting of caproic acid, oenanthic acid, caprylic acid, pelargonic acid, capric acid, undecanoic acid, lauric acid, tridecanoic acid, myristic acid, pentadecanoic acid, palmitic acid, heptadecanoic acid, stearic acid, undecenoic acid, lauroleic acid, myristoleic acid, palmitoleic acid, petroselic acid, petroselaidic acid, oleic acid, elaidic acid, linoleic acid, linolaidic acid, linolenic acid or technical mixtures thereof. It is preferred to use fatty acids of vegetable or animal origin which may be partly or completely hydrogenated. Hydrogenated coconut oil fatty acid is particularly preferred.

The starting compounds, fatty acid (II) and ammonium hydroxyalkanesulfonate (I), may be used in any ratios although they are preferably used in a molar ratio of 0.8–1.8 : 1 and more preferably in a molar ratio of 0.9–1.1 : 1.

The esterification catalyst may be added to the reaction mixture at any time before the reaction and is preferably added together with the ammonium hydroxyalkanesulfonate. The catalyst is added to the reaction mixture in a quantity of 0.02 to 1.5% by weight and preferably in a quantity of 0.03 to 0.1% by weight, based on the starting compounds. Catalysts suitable for use in the process according to the invention are any of the usual esterification catalysts. Preferred catalysts are strongly acidic catalysts, such as alkylsulfonic acids and alkylbenzenesulfonic acids; tin compounds, such as for example tin(II) oxide, tin(II) oxalate, dibutyl tin(IV) diacetate, dibutyl tin(IV) dilaurate; inorganic zinc compounds, such as zinc oxide, zinc sulfate, zinc sulfonate, zinc isethionate and zinc oxide acidified with sulfamic or sulfuric acid. Methanesulfonic acid, ethanesulfonic acid and isethionic acid are particularly preferred. It has been found that the pH value of the reaction mixture is reduced by the use of strongly acidic catalysts, preferably to pH 2–4, so that the formation of free ammonia in the reaction mixture is avoided. The isethionic acid preferably used may be obtained from aqueous sodium isethionate solution or from aqueous ammonium isethionate solution in an H+-charged ion exchanger. In one particularly preferred embodiment, the exchange is coupled with the direct introduction of the catalyst solution into the reactor.

A stabilizer such as, for example, hypophosphorous acid, $H_3PO_2$, or phosphorous acid, $H_3PO_3$, may be added to the reaction mixture. It has been found that the reaction product remains light in color, even in the presence of strongly acidic esterification catalysts, when a stabilizer is used. The stabilizer reduces any color-forming substances by oxidation. The stabilizer may be mixed with the fatty acid before the drying step.

In the process according to the invention, the reactants are dried before the beginning of the reaction. To this end, the ammonium hydroxyalkanesulfonate corresponding to general formula (I) and the fatty acid or fatty acid mixture corresponding to formula (II) are initially introduced into the reaction vessel and heated to a temperature of 120° C. to 160° C. In one preferred embodiment of the invention, the fatty acid or the fatty acid mixture is first introduced into the reaction vessel and heated to a temperature of 120° C. to 160° C. after which the pressure is reduced to 100 to 700 mbar and the ammonium hydroxyalkanesulfonate is introduced into the hot fatty acid. The water present, more particularly the water of solution present where aqueous solutions are used, is removed at the temperature mentioned above and under a pressure of 100 mbar to 700 mbar, preferably under a pressure of 150 mbar to 300 mbar and more preferably under a pressure of 150 mbar to 200 mbar. The temperature should not be too high because, at overly high temperatures, the reactants are in danger of reacting with one another during the drying step. It has surprisingly been found that, in a vacuum, the main reaction takes place without foaming providing all the water of solution is removed before the reaction and no reaction takes place during the drying step. On the other hand, it has been found that, if the water is not completely distilled off during the drying step or if the reaction has started during the drying step, the main reaction is accompanied by intensive foaming of the product, in some cases even into the vacuum system. Once the reaction mixture has foamed, the reaction rate falls considerably.

After drying, the reaction mixture consisting of starting compounds, catalyst and optionally stabilizer is heated to a temperature above 160° C. The reaction temperature is preferably in the range from 165° C. to 195° C. and more preferably in the range from 175° C. to 190° C. In order to displace the reaction equilibrium towards the reaction product as the reaction approaches its conclusion, the temperature is increased as far as possible, preferably to 180° C. to 195° C. In order to minimize or completely avoid the decomposition of the starting compounds and the reaction product and the formation of secondary products, the temperature should not exceed 200° C.

In order to displace the reaction equilibrium towards the reaction product, the water formed is directly removed from the reaction mixture. In the interests of more effective removal of water by distillation, the pressure prevailing during the esterification reaction is in the range from 250 mbar to atmospheric pressure, preferably in the range from 350 to 550 mbar and more preferably in the range from 400 to 500 mbar. At lower pressures, the system is in danger of intensive foaming with a significant increase in volume and a reduction in heat transfer.

Since the reaction products easily decompose by oxidation with air at temperatures above about 100° C., one particular embodiment of the invention is characterized by the introduction of an inert gas, more particularly nitrogen, into the reaction system. It is particularly preferred to introduce the inert gas into the reaction mixture from below and in addition onto the surface of the product. Darkening of the product can also be avoided in this way. However, it is important to ensure that only a minimal quantity of nitrogen is introduced because otherwise the fatty acid used could also be driven out.

The reaction is able to follow a particularly uniform course if the reaction mixture is intensively mixed during the heating phase, the drying step and the reaction, preferably using a suspension-type stirrer and, more preferably, an upwardly transporting suspension-type stirrer.

Particularly effective mixing is obtained during drying and during the reaction if the reaction mixture is additionally pump-circulated, preferably through a heated, externally arranged falling-film evaporator. The effect of using a stirrer and pump-circulating the reaction product is that a homogeneous reaction mixture is formed as a result of intensive mixing and sudden delays in boiling of the reaction mixture are avoided. An externally arranged falling-film evaporator also affords the advantage that the reaction zone is additionally extended because the condensation reaction can take place in the falling-film evaporator itself, even during circulation of the reaction mixture. A falling-film evaporator is also preferably used to drive out the water of reaction.

The water removed from the reaction mixture is condensed in condensers connected to the reaction vessel. In one possible procedure, the fatty acid corresponding to formula (II) distilled off during the reaction together with the water of reaction is condensed in a first condenser, preferably a dephlegmator, in dependence upon the pressure at a temperature of 120° C. to 150° C. and returned to the reaction vessel. The fatty acid which is not condensed in the first condenser may then be condensed in a second condenser together with the water of reaction at a temperature of 40° C. to 70° C., separated from the water phase in a following phase separator and likewise returned to the reactor.

The selective condensation of the fatty acid corresponding to formula (II) in the first condenser on the one hand relieves the load on the second condenser in which the water is condensed and, on the other hand, ensures that the fatty acid does not collect in the pipes and on the heat exchange surfaces of the condenser and the phase separator — which would result in blockages — at relatively low temperatures at which the water is also condensed. In addition, the use of a first condenser, more particularly a dephlegmator, has the advantage that only a very small percentage of fatty acid is present outside the reaction vessel and a large excess of fatty acid is present in the reactor itself, so that inter alia the reaction mixture remains low in viscosity. To ensure that as little unreacted fatty acid corresponding to formula (II) as possible is present outside the reactor, more particularly in the second condenser, water may be introduced beforehand into the phase separator so that the lighter fatty acid corresponding to formula (II) may be directly returned to the reactor. If an aqueous solution of the ammonium hydroxyalkanesulfonate is used, there is no need to introduce water into the phase separator beforehand because water collects therein during the heating and drying phase before the beginning of the reaction at relatively low temperatures.

In one preferred embodiment, the pressure is reduced to 60 to 200 mbar and preferably to 100 to 165 mbar towards the end of the reaction, i.e. after most of the water and preferably more than 80% of the water has been removed. By reducing the pressure, the remaining water is removed, the conversion of the ammonium hydroxyalkanesulfonate simultaneously being increased once more in a form of after-reaction by displacement of the equilibrium. The pressure is reduced as slowly as possible in order uniformly to remove the water of reaction so that the reaction mixture does not foam. If intensive foaming is observed during reduction of the pressure, making any further reduction of the pressure impossible, this may be taken as a sign that the reaction conversion is still below 80%. After removal of the water, the actual condensation reaction is terminated.

On completion of the condensation reaction, the acidic catalyst is neutralized with a base. The neutralization of the reaction mixture is preferably carried out at a temperature below 180° C. to avoid discoloration of the reaction product. Suitable neutralization bases are alkali metal hydroxides, such as sodium, potassium and lithium hydroxide, alkaline earth metal oxides and hydroxides, such as magnesium oxide, magnesium hydroxide, calcium oxide and calcium hydroxide, alkali metal carbonates and hydrogen carbonates, such as sodium carbonate and sodium hydrogen carbonate, alkaline earth metal carbonates, such as calcium carbonate, ammonia, mono-, di- and tri-$C_{2-4}$-alkanolamines, for example mono-, di- and triethanolamine, and also primary, secondary or tertiary $C_{1-4}$ alkylamines.

After cooling, the reaction product obtained in the condensation reaction may be further processed as such. For example, the product may be completely dried and further processed as a powder. In one preferred embodiment, an aqueous solution of ammonium fatty acid hydroxyalkanesulfonate is prepared and may then be directly used for the production of detergents for example. Solutions such as these preferably have an ammonium fatty acid hydroxyalkanesulfonate content of 1 to 35% by weight and preferably 20 to 30% by weight. To prepare an aqueous solution, the cold water is rapidly added to the hot reaction mixture. In another embodiment, the hot reaction mixture is introduced into the cold water.

In one particularly preferred embodiment, the pressure in the reactor is increased to a value of 1 to 5 bar before the water is added. The water is then added under pressure. Where this procedure is adopted, foaming of the reaction mixture is avoided and the temperature of the mixture quickly falls to 60° C. to 80° C. Cooling the reaction mixture under pressure not only avoids foaming, high heat transfer is also obtained with the low-viscosity aqueous solution. The solution may then be rapidly cooled to below 50° C. which minimizes the danger of hydrolysis at relatively high temperatures.

In another particularly preferred embodiment, the base is added to the reaction mixture in two portions. In the first step, the base is only added in the quantity required to neutralize the acidic catalyst. The second portion is mixed with the water of solution and is added to the solution therewith as described above for the addition of water. The second portion is essentially added to adjust the pH value. The aqueous solution preferably has a pH value of 6.3 to 7.1 and, more preferably, a pH value of 6.5 to 6.8. It is important to ensure that the pH value is not too low because otherwise the ester could be hydrolyzed. On the other hand, if the pH value is too high, free ammonia is formed which has an adverse effect on the odor of the reaction mixture and which forms amides with the free fatty acids.

To improve the color of the products obtained, typical bleaching agents may be added to the reaction product or to the solution prepared in order to improve the color and to minimize the odor of any hypophosphorous acid present. $H_2O_2$ is preferably used as the bleaching agent in a quantity of 0.005 to 1.5% by weight. The stability of the products obtained in storage can be improved by addition of typical stabilizers, more particularly antioxidants and UV stabilizers. Such stabilizers may be added to the reaction product or to the solution prepared in a quantity of 0.001% by weight to 3% by weight. Suitable stabilizers are, for example, hypophosphorous acid, phosphorous acid, phosphoric acid or phosphoric acid esters which may be used in quantities of 0.005 to 0.1% by weight.

Finally, the cooled solution may be filtered to remove esters of ethylene glycol precipitated at low temperatures and free fatty acids from the mixture. The mixture is preferably filtered through a 5 to 10 μm filter.

EXAMPLES

Example 1

124 kg of hydrogenated coconut oil fatty acid were introduced with 0.4 kg of 50% hypophosphorous acid ($H_3PO_2$) into and heated to 155° C. in a 600 l esterification reactor blanketed with an inert gas. 134 kg of 60% ammonium isethionate solution were introduced into the reactor together with 0.21 kg of methanesulfonic acid under a pressure of 165 mbar and the water of solution was distilled off.

After the addition, the pressure was increased to 400 mbar and the reaction mixture was heated to 175° C. to 190° C. Most of the water of reaction was distilled off in the main reaction with intensive refluxing and condensed in the condenser. The fatty acid distilled off with the water of reaction was partly condensed in the preceding dephlegmator and returned to the reactor. To improve the color of the product and the distillation conditions, nitrogen gas was introduced into the product.

After most of the water of reaction had distilled off, the pressure was reduced in steps to 135 mbar in the after-reaction.

On completion of the reaction, the reaction mixture was cooled to a temperature below 180° C. and the strongly acidic catalyst was neutralized to a pH value above 4 with 1.6 kg of triethanolamine. The pressure was 800 mbar.

To adjust the aqueous solution, the pressure in the reactor was adjusted to more than 2 mbar with nitrogen and 341 kg of water were quickly introduced into the reactor together with 5.5 kg of triethanolamine. In 6 minutes, the temperature in the reactor fell to below 70° C. The solution was pump-circulated into a receiving vessel in which it was further cooled. A 30% solution was adjusted by addition of 125 kg of water and was bleached with 0.5 kg of $H_2O_2$ and subsequently filtered.

|  | Reaction product (% by weight) | Solution (% by weight) |
| --- | --- | --- |
| Ammonium fatty acid isethionate | 87.4 | 25.6 |
| Ammonium isethionate | 3.7 | 0.8 |
| Free fatty acid | 5.5 | 1.3 |
| Water | 0 | 70 |
| Triethanolamine |  | 0.8 |
| Epton | 85.9 | 25.2 |
| pH | — | 6.5 |

Example 2

94 kg of hydrogenated coconut oil fatty acid were introduced together with 0.3 kg of 50% hypophosphorous acid ($H_3PO_2$) into and heated to 160° C. in a 600 liter esterification reactor blanketed with an inert gas. 111 kg of 60% ammonium isethionate solution were introduced into the reactor together with 0.15 kg of isethionic acid under a pressure of 165 mbar and the water of solution was distilled off. The isethionic acid was obtained from Na isethionate in a preceding H-ion exchanger.

After the addition, the pressure was increased to 400 mbar and the reaction mixture was heated to 175° C. to 190° C. Most of the water of reaction was distilled off in the main reaction with intensive refluxing and condensed in the condenser. The fatty acid distilled off with the water of reaction was partly condensed in the preceding dephlegmator and returned to the reactor. To improve the color of the product and the distillation conditions, nitrogen gas was introduced into the product.

After most of the water of reaction had been distilled off, the pressure was reduced in steps to 135° C. in the after-reaction.

On completion of the reaction, the reaction mixture was cooled to a temperature below 180° C. and the strongly acidic catalyst was neutralized to a pH value above 4 with 1.1 kg of triethanolamine. The pressure was 800 mbar.

To adjust the aqueous solution, 284 kg of water were introduced together with 4.1 kg of triethanolamine into the receiving vessel. The reaction mixture was introduced under nitrogen pressure into the water/triethanolamine. The system rapidly cooled without intensive foaming. To remove residues of reaction product from the reactor, the aqueous solution was pumped back into the reactor after cooling and the reactor was rinsed with the solution. A 30% solution was adjusted by addition of 94 kg of water and was bleached with 0.5 kg of $H_2O_2$ and subsequently filtered.

|  | Reaction product (% by weight) | Solution (% by weight) |
| --- | --- | --- |
| Water | — | 70.7 |
| Triethanolamine |  | 1.0 |
| Epton | 82.5 | 24.4 |
| pH | — | 7.1 |

What is claimed is:

1. A process for the production of ammonium fatty acid hydroxyalkanesulfonates in which (a) ammonium hydroxyalkanesulfonate corresponding to general formula (I):

$$HO-(C_nH_{2n})-SO_3NH_4 \qquad (I)$$

wherein n=2 to 4, is subjected to the esterification reaction with a fatty acid corresponding to the formula (II)

$$R-COOH \qquad (II)$$

wherein RCO is an aliphatic, linear or branched acyl radical containing 6 to 18 carbon atoms, in the presence of an esterification catalyst, characterized in that (a) before the esterification reaction, the starting compounds corresponding to formulae (I) and (II) are dried at a temperature of 120° C. to 160° C. and under a pressure of 100 to 700 mbar; (b) the esterification reaction is carried out at a temperature above 160° C. to 195° C. and under a pressure of 250 mbar to atmospheric pressure; (c) water of solution and water of reaction formed are directly removed from the reaction mixture; (d) the catalyst is neutralized with a base on completion of the reaction.

2. The process of claim 1 characterized in that ammonium isethionate is used as the compound corresponding to formula (I).

3. The process of claim 1 characterized in that hydrogenated fatty acid is used as the compound corresponding to formula (II).

4. The process of claim 1 characterized in that the fatty acid corresponding to formula (II) and the ammonium hydroxyalkanesulfonate corresponding to formula (I) are present in a molar ratio of 0.8–1.8:1.

5. The process of claim 1 characterized in that a stabilizer is added to the reaction mixture.

6. The process of claim 1 characterized in that alkanesulfonic acids are used as the catalyst.

7. The process of claim 6 characterized in that isethionic acid is produced from an aqueous isethionate solution via an ion exchanger.

8. The process of claim 1 characterized in that the drying step is carried out under a pressure of 150 to 300 mbar.

9. The process of claim 1 characterized in that the esterification reaction is carried out under a pressure of 350 to 500 mbar.

10. The process of claim 1 characterized in that an inert gas is introduced into the reactor.

11. The process of claim 1 characterized in that sodium hydroxide, alkali metal carbonates, hydrogen carbonates, alkaline earth metal carbonates, triethanolamine or trimethanolamine are used as the base.

12. The process of claim 1, characterized in that a defined quantity of water is added to the reaction mixture after neutralization.

13. The process of claim 1 characterized in that the base is added in two portions, the first portion of the base being directly added to the reaction mixture in undiluted form on completion of the reaction and the second portion being thereafter added in admixture with water.

14. The process of claim 12 characterized in that the aqueous solution is treated with a bleaching agent.

15. The process of claim 2 characterized in that the ammonium isethionate is in the form of a 50 to 65% by weight solution.

16. The process of claim 3 characterized in that the hydrogenated fatty acid is hydrogenated coconut oil fatty acid.

17. The process of claim 4 characterized in that the fatty acid corresponding to formula (II) and the ammonium hydroxyalkanesulfonate corresponding to formula (I) are present in a molar ratio of 0.9–1.1:1.

18. The process of claim 5 characterized in that the stabilizer is hypophosphorous acid.

19. The process of claim 6 characterized in that said alkanesulfonic acids are methanesulfonic acid or isethionic acid.

20. The process of claim 10 characterized in that said inert gas is nitrogen.

* * * * *